United States Patent [19]
Claren et al.

[11] Patent Number: 6,024,753
[45] Date of Patent: Feb. 15, 2000

[54] DEVICE FOR STAUNCHING UTERUS BLEEDING

[75] Inventors: Jan Claren, Lund; Ulf Ulmsten, Danderyd, both of Sweden

[73] Assignee: Atos Medical AB, Horby, Sweden

[21] Appl. No.: 09/117,757

[22] PCT Filed: Feb. 4, 1997

[86] PCT No.: PCT/SE97/00162

§ 371 Date: Dec. 24, 1998

§ 102(e) Date: Dec. 24, 1998

[87] PCT Pub. No.: WO97/27810

PCT Pub. Date: Aug. 7, 1997

[30] Foreign Application Priority Data

Feb. 5, 1996 [SE] Sweden .................................. 9600407

[51] Int. Cl.$^7$ .................................................. A61M 29/00
[52] U.S. Cl. ............................................. 606/193; 604/55
[58] Field of Search ..................... 606/193, 108, 606/119; 604/55, 96, 178

[56] References Cited

U.S. PATENT DOCUMENTS

| | | | |
|---|---|---|---|
| 4,552,557 | 11/1985 | Rangaswamy . | |
| 5,372,584 | 12/1994 | Zink et al. | 606/193 |
| 5,409,496 | 4/1995 | Rowden et al. | 606/193 |
| 5,624,399 | 4/1997 | Ackerman | 606/193 |

FOREIGN PATENT DOCUMENTS

| | | |
|---|---|---|
| 0141589 | 10/1984 | European Pat. Off. . |
| 3805368 | 2/1988 | Germany . |
| 19525926 | 7/1995 | Germany . |
| 9507664 | 3/1995 | WIPO . |
| 9727810 | 8/1997 | WIPO . |

*Primary Examiner*—Michael Buiz
*Assistant Examiner*—Kevin Truong
*Attorney, Agent, or Firm*—James Ray & Associates

[57] ABSTRACT

A device for staunching uterine bleeding comprising an expandable balloon and a tubular handle connected therewith for the insertion of the balloon into the uterine cavity, which can be connected to a fluid source for pressurizing the balloon to effecting and maintain the expansion thereof. The balloon is dimensioned to fill the uterine cavity at expansion and to exert pressure against the bounding wall thereof over substantially the total surface of the wall. The device further includes a pump and control unit and a hose connected to one end thereof with the handle at the other end thereof with a connection element for connecting to a fluid source. The hose can be detachable mounted to the pump and control unit in operative co-operation therewith and forms together with the balloon and the handle a separate unit for one-way use.

22 Claims, 4 Drawing Sheets

DEVICE FOR STAUNCHING UTERUS BLEEDING

BACKGROUND OF THE INVENTION

1. Field of the Invention

The invention relates to a device for staunching uterine bleeding comprising an expandable balloon and a tubular handle connected therewith for the insertion of the balloon into the uterine cavity, a hose for connecting the balloon to a fluid source, and means for supplying fluid under pressure to the balloon to effect and maintain the expansion thereof, the balloon being dimensioned to fill the uterine cavity at expansion and to exert pressure against the bounding wall thereof over substantially the total surface of said wall.

2. Description of the Related Art

EP-A1-0 141 589 discloses a device of this kind which comprises a semi-rigid flexible rubber tube and an expandable balloon of elastic foldable material, which is connected to the tube and can be expanded by pressurized fluid, gas or liquid, being supplied to the balloon through the tube. In the prior art device the tube forms a handle for the insertion of the balloon into the uterine cavity.

BRIEF SUMMARY OF THE INVENTION

The purpose of the invention is to provide a device for staunching uterine bleeding, which can be used easily and allows the treatment to be performed at great safety in hygienic and operative respect in order to staunch uterine bleeding also under severe conditions, and which allows accurate adjustment to varying probe measures as well as control of the pressure in the balloon at contraction of uterus while an hemostatic effect being maintained over the total bounding surface of the uterine cavity.

This is achieved by providing a device for staunching uterine bleeding which is of the kind referred to above and according to the invention has obtained the characterizing features of claim 1.

BRIEF DESCRIPTION OF THE SEVERAL VIEWS OF THE DRAWINGS

In order to explain the invention in more detail an illustrative embodiment of the device will be described reference being made to the accompanying drawings in which.

DETAILED DESCRIPTION OF THE INVENTION

Figure 1:
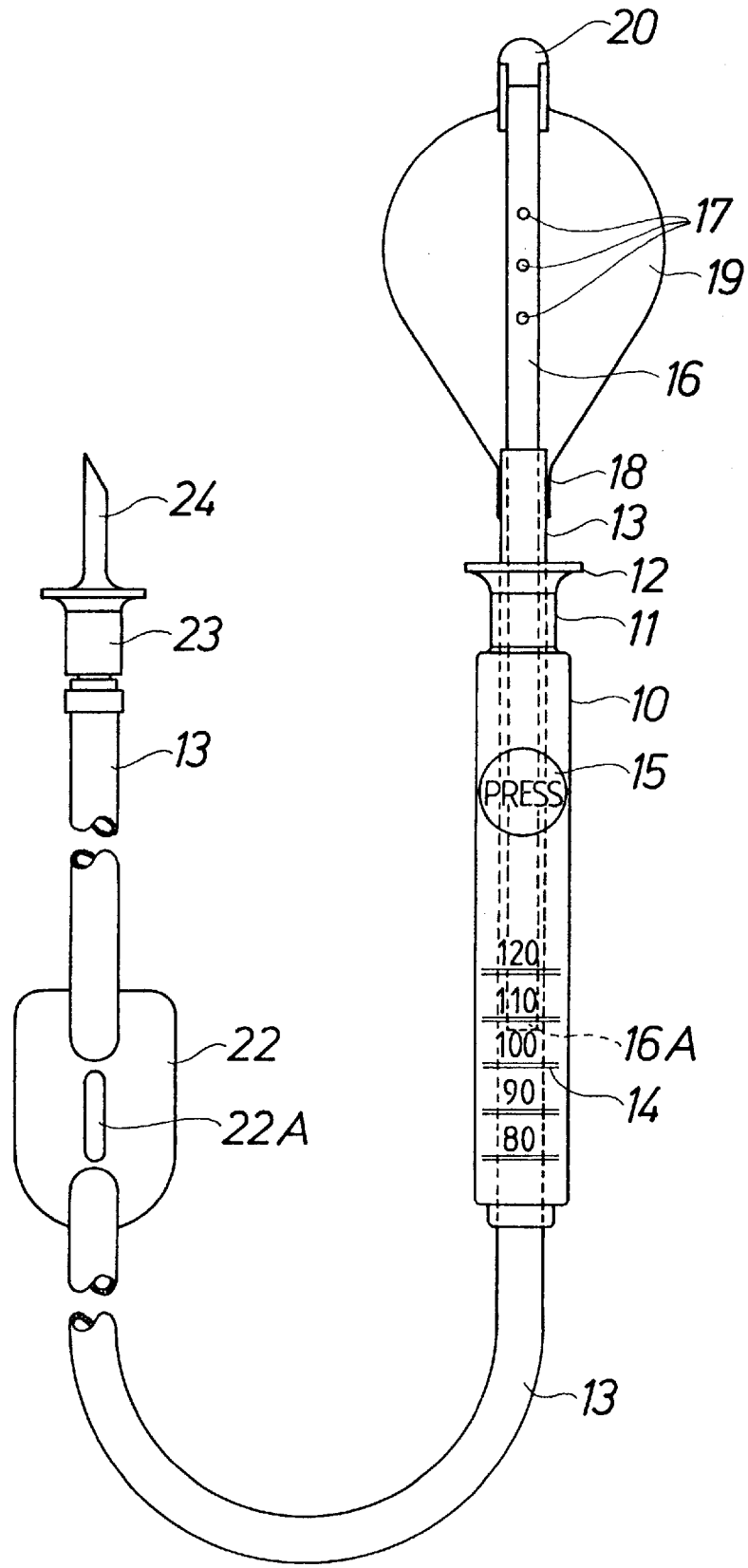
FIG. 1 is a plan view of a balloon and hose unit forming part of the device.
Figure 2:
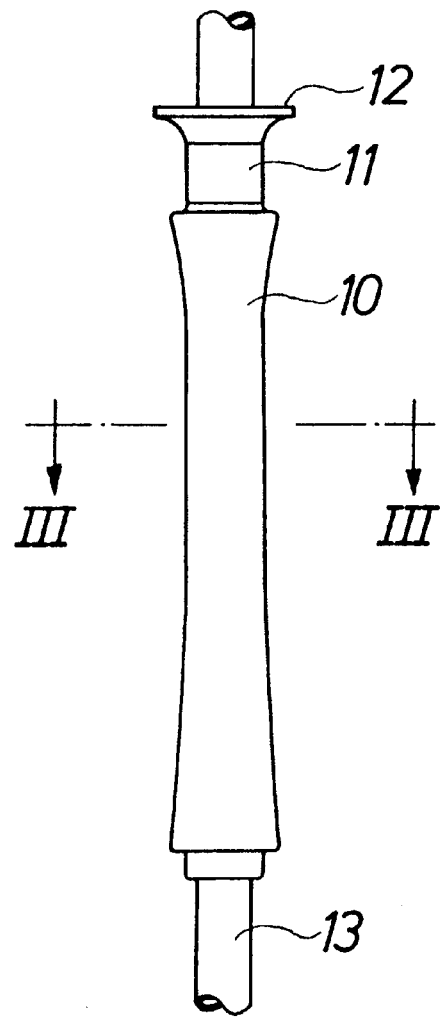
FIG. 2 is a fragmentary side view of a handle in the balloon and hose unit.
Figure 3:
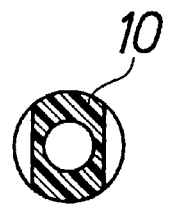
FIG. 3 is a cross-sectional view of the handle along line III—III in FIG. 2.

The balloon and hose unit disclosed in the drawings FIGS. 1–3 comprises a tubular handle 10 of translucent or transparent soft plastic or another comparable material, which is easy to grip and forms flat upper and lower sides and curved side surfaces as will be seen from FIG. 3. At one end the handle forms a socket 11 having a outwardly flaring end portion 12. A hose 13 which consists preferably of silicone rubber (medical quality) or another comparable material and for reasons which will appear below preferably is translucent or transparent is pushed through the handle and the socket and projects therefrom at the flaring portion. The hose is glued to the handle. A scale 14 is provided on the upper side of the handle, and on this side there is also indicated a circular field 15 with legend PRESS.

A tube 16 which preferably consists of plastic or rubber of medical quality such as polyethylene (LE6601-PH) and is relatively stiff but nevertheless can be bent and can maintain temporarily the bent shape is partly inserted into hose 13 through the end thereof which protrudes from socket 11 and can be displaced axially in relation to the hose and thus in relation to the handle. The tube can have a colour which contrasts with the colour of the handle, and the position of the inner end 16A of the tube, which as a consequence thereof can be easily seen through the handle can be read at scale 14. In FIG. 1 the end is substantially at 107 on the scale. By pressing the thumb against pressure field 15 on the handle pressure can be exerted against tube 13 by deformation of the handle and the hose therein and thus the tube can be arrested in a desired displaced position in relation to the hose and the handle by frictional engagement between the hose and the tube. To the end of hose 13 projecting from the handle there is attached at 18 a balloon 19 which is attached also to a plug 20 which is attached to and closes the outer end of tube 16. Thus, tube 16 is completely enclosed by the balloon, and apertures 17 open in the interior of the balloon. Preferably, the balloon consists of thin silicone rubber (medical quality) or another comparable elastically extendible and/or foldable material such as polyurethane.

Hose 13 via a pressure cell 22 having a finger grip 22A is connected with an end piece 23 having a connection spike 24 i.e. a tube integral with the end piece, which has a point at the free end thereof formed by the tube being obliquely cut. The unit formed by the end piece and the connection spike preferably is made of ABS or another comparable material and is available on the market under the term plastic cannula.

Figure 4:
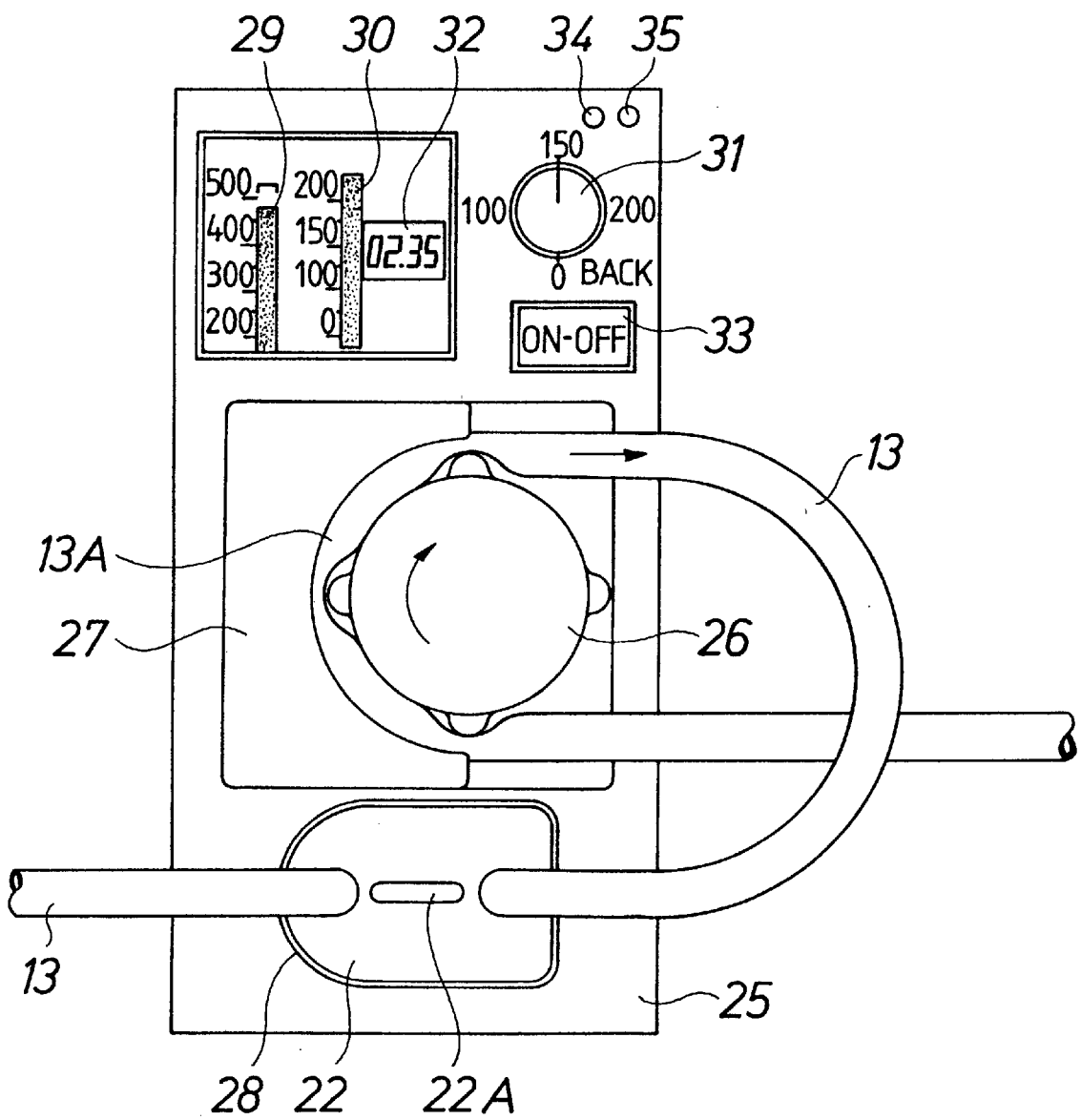
FIG. 4 is a plan view of a pump and control unit forming part of the device for supply of liquid to the balloon.

The balloon and hose unit now described according to the invention shall be operatively combined with the pump and control unit shown in FIG. 4, and it shall be made as a one-way product i.e. it shall be delivered in a sterile package and it shall be scrapped after a single use.

The pump and control unit shown in FIG. 4 can be battery operated and is intended to be placed on a support (a bed or a table) but it can also be provided with means for suspending the same on a drop stand. Said unit comprises a control box 25 wherein there is mounted an electric drive motor for a rotor 26 of a peristaltic pump said rotor being mounted on the upper side of the control box. A loop 13A formed by hose 13 is applied around rotor 26, as shown, and is kept engaged with half the circumference of the rotor by a stationary guide 27 in order to operatively co-operate with the rotor and to form together with the rotor a peristaltic pump. In the upper side of the control box a depression 28 is provided which fits the pressure cell 22 which is located in the depression having at the bottom thereof a pressure sensor (not shown) for sensing the pressure in the pressure cell. In the control box there are means for measuring volume with an associated volume indicator 29, and for measuring pressure with an associated pressure gauge 30 indicator and gauge being located on the upper side of the control box where there is also a knob 31 for setting a nominal value of the pressure and a time indicator 32. Moreover, there is on the control box a button 33 for switching the pump and control unit on and off as well as indicator lamps 34 and 35.

Control box 25 shall also contain the electronic system required for controlling functions in connection with the use of the device, which shall be performed automatically without any action from the operator. At the state of the art in the field of electronics such an electronic system can be proposed by the average man skilled in the art and, therefore, it will not be described in more detail here.

When the device described is to be used in order to provide a hemostatic effect in the uterine cavity when this is bleeding cannula 23, 24 should be connected to a fluid source which can comprise a plastic bag with physiological salt solution; the cannula is easily put into the connection socket on the bag while penetrating the membrane closing said socket. Hose 13 and pressure cell 22 should be placed in the pump and control unit in the manner disclosed in FIG. 4. With balloon 19 in the deflated condition the operator grips handle 10 and presses against pressure field 15 so that tube 16 will be arrested in a protruding position. The tube with the enclosing balloon 19 is now inserted into the uterine cavity via vagina and cervix, the tube forming directional means at the insertion which can be further facilitated by the possibility of permanently bending the tube. When plug 20 engages the distal wall of uterus, which the operator feels or can investigate by means of X-ray if plug 20 and possibly also tube 16 contains radio opaque material, the tube is released by the operator relieving the pressure against pressure field 15. The handle can now be displaced in relation to tube 16 which will stand stationary due to the engagement of the plug against the wall of the uterine cavity, until the flanged portion 12 engages cervix. In this position the distance from the end of plug 20 to the flanged portion 12 represents the so called probe measure, and scale 14 on handle 10 indicates this measure which can be red against the scale at end 16A of the tube, said end being visible through the handle and the hose.

The pump and control unit is switched on by means of button 13, and then signal lamp 34 will be lit up. A nominal value of the pressure to be maintained in balloon 19 during the hemostatic treatment of the uterine cavity is set by means of knob 31. Rotor 26 starts rotating clockwise as indicated by an arrow in FIG. 4, and liquid will be sucked from the liquid source and will be supplied under pressure to the interior of balloon 19 via hose 13, pressure cell 22, handle 10, tube 16, and apertures 17. The flow direction of the liquid is indicated by an arrow in FIG. 4. The pressure of the liquid supplied is sensed by the pressure sensor via pressure cell 22. During the supply of liquid the balloon 19 will be expanded under elastic extension or by smoothing away existing folds, respectively, until the balloon completely fills the uterine cavity and engages the wall thereof. As liquid is being supplied the pressure against the wall will be increased, and this pressure is identical with the pressure sensed by the pressure sensor and indicated by pressure gauge 30. When the nominal value set has been reached the pump will be stopped so that the supply of liquid will cease. The attainment of the nominal value of the pressure is indicated by signal lamp 35 being lit up. Volume meter 29 indicates the amount of liquid that has been supplied to the balloon, and this meter should be of the type which maintains the indication of the largest volume reached even if the volume then should decrease, the meter at the same time indicating the actual liquid volume.

The balloon is kept pressurized as long is deemed necessary for the hemostatic treatment of uterus. During the treatment uterus may contract which normally happens after a birth but also may be initiated by medical treatment, and such contraction means of course that the pressure will increase. By automatic control in the electronic system the pump will then be started again but is now allowed to operate in the opposite direction for draining liquid from the balloon until the set nominal value of the pressure has again been reached. The volume meter now indicates the volume of liquid present in the balloon for the time being the indication of the original volume of liquid at the same time being maintained. During the treatment tube 16 can be freely moved in handle 10, and at the contraction of uterus the tube will be pressed into the handle and will indicate on scale 14 the reduced probe measure existing after contraction, which is important information for the operator at the treatment. The period over which the treatment is going on is indicated on time indicator 32, and when the necessary treatment period has been reached knob 31 will be set on the nominal value zero or in a reverse position the balloon then being emptied completely by the pump operating in counterclockwise direction and pumping the liquid back to the liquid source. The balloon is withdrawn from uterus, and the balloon and hose unit is separated from the pump and control unit and is scrapped.

In the embodiment disclosed there is provided a peristaltic pump but it is within the scope of the invention to provide a pump of another kind to which the balloon and hose unit is connected.

The pump can also comprise a pressure cuff which encircles the bag containing physiological salt solution and is provided with a manometer and a degassing valve. When liquid is supplied to the balloon the pressure cuff is pressurized until the liquid is under the desired pressure, and when the pressure of the fluid is increased due to contraction of uterus air is discharged from the pressure cuff until the desired pressure has been restored.

Figure 5:
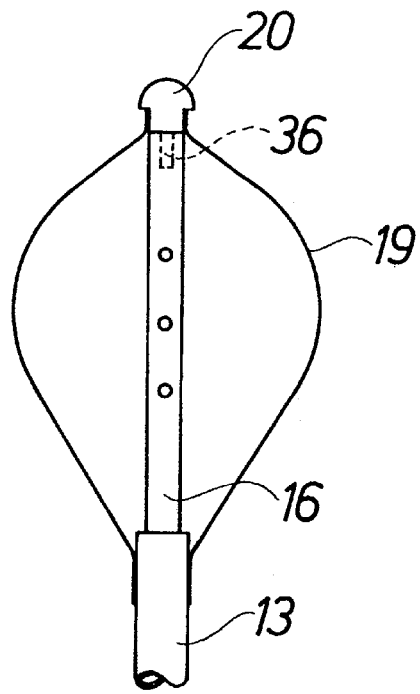
FIG. 5 is a fragmentary plan view of a modified embodiment of the balloon and hose unit of the device.
Figure 6:
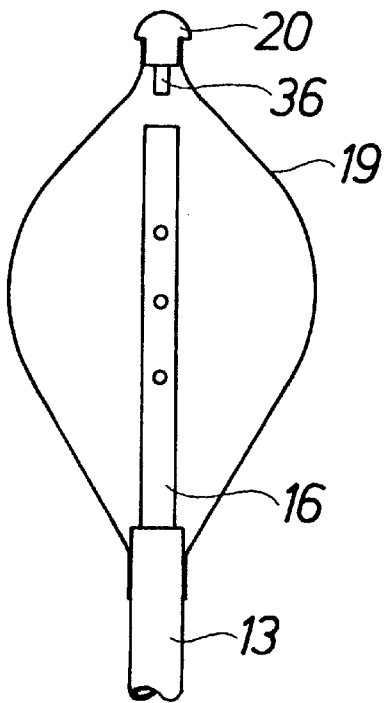
FIG. 6 is a view corresponding to FIG. 5 with the balloon further expanded.

In FIGS. 5 and 6 there is shown a modified embodiment of the balloon. In this case tube 16 is attached to hose 13 and plug 20 is detachably connected with the tube by being inserted into the tube at a pin 36, FIG. 5. The pin has such fit in the tube that the plug at a predetermined pressure in the balloon will be pressed out of the tube, FIG. 6, so that the balloon can completely freely adapt itself to the shape of uterus. Instead of being provided with a pin the plug may form a socket fitting over the outside of tube 16. The pin can also be so long, without covering apertures 17, that the plug is always guided in the tube.

We claim:

1. Device for staunching uterine bleeding comprising an expandable balloon and a tubular handle connected therewith for the insertion of the balloon into the uterine cavity, a hose for connecting the balloon to a fluid source, and means for supplying fluid under pressure to the balloon to effect and maintain the expansion thereof, the balloon being dimensioned to fill the uterine cavity at expansion and to exert pressure against the wall defining said cavity over substantially the total surface of said wall, wherein the device comprises also a control unit including said means for supplying fluid under pressure, and a pressure gauge, the hose at one end thereof is passed through the handle and connected with the balloon, and at the other end thereof has a connector for connection to the fluid source, and said hose together with the balloon the handle and the connector forms a separate unit for one-way use.

2. Device as in claim 1, wherein said means for supplying fluid under pressure comprises a motor driven rotor which together with said hose forms a peristaltic pump.

3. Device as in claim 2, wherein said control unit comprises means for controlling the rotation of the rotor in dependence of indicated pressure.

4. Device as in claim 1, wherein said means for supplying fluid under pressure comprises a pressure cuff with air pump, the pressure cuff encircling a flexible liquid container to be connected to the hose.

5. Device as in claim 1, wherein a proximal end of the balloon is connected with the handle while a distal end thereof can be displaced in relation to the handle.

6. Device as in claim 5, wherein a distal end of the balloon is connected with an outer closed end of a tube projecting from the handle, said tube being connected to the hose and being perforated to communicate with the interior of the balloon.

7. Device as in claim 6, wherein one end of the tube is guided for axial displacement in the handle.

8. Device as in claim 7, wherein the tube can be arrested in the handle.

9. Device as in claim 8, wherein the handle is of an elastically deformable material for transferring manual pressure against the handle to the tube (16) for arresting the tube by frictional engagement.

10. Device as in any of claims 7–9, wherein the handle is translucent or transparent for determination of the displaced position of the tube by ocular observation of the position of a tube end positioned in the handle, in relation to a scale provided on the handle.

11. Device as in claim 10, wherein the tube at least at said tube end has a color contrasting with that of the handle.

12. Device as in claim 6, wherein the tube at said outer end thereof is closed by means of a plug which is detachably provided on or in the tube end.

13. Device as in claim 12, wherein the plug is displaceably guided in the tube.

14. Device as in claim 6, wherein the tube can be plastically bent at least partly.

15. Device as in claim 1, wherein the hose and balloon unit comprise a pressure cell in the hose which can be detachably mounted on said control unit for operative cooperation with a pressure sensor provided therein.

16. Device as in claim 1, wherein said control unit comprises means (29, 30) for indicating the amount of fluid supplied to the balloon (19).

17. Device as in claim 1, wherein the balloon consists of an elastic material to expand under elastic extension thereof.

18. Device as in claim 1, wherein the balloon is folded to expand while the folds are being smoothed away completely or partly.

19. Device for staunching uterine bleeding comprising an expandable balloon; a tubular handle for insertion of the balloon into the uterine cavity, a proximal end of the balloon being connected with tubular handle; a hose connected at one end thereof with the tubular handle; a tube displaceably received by the tubular handle and projecting therefrom, a distal end of the balloon being connected with an outer closed end of said tube extending into the balloon and communicating with the interior thereof through a perforation of the tube; a connector at the outer end of the hose; a control unit including means for supplying fluid under pressure, and a pressure gauge for measuring the pressure of the fluid supplied, said connector being connected to said control unit for delivery of fluid under controlled pressure to the balloon to effect and maintain the expansion thereof, the balloon being dimensioned to fill the uterine cavity at expansion and to exert pressure against the wall defining said cavity over substantially the total surface of said wall, said hose together with the balloon, the handle, the tube, and the connector forming a separate unit for one-way use.

20. Device as in claim 19, wherein the tube can be arrested in the handle.

21. Device as in claim 20, wherein the handle is of an elastically deformable material for transferring manual pressure against the handle to the tube for arresting the tube by frictional engagement.

22. Device as in claim 21, wherein the handle is translucent or transparent for determination of the displaced position of the tube by ocular observation of the position of a tube end positioned in the handle, in relation to a scale provided on the handle.

* * * * *